(12) United States Patent
Tengler

(10) Patent No.: US 10,874,741 B2
(45) Date of Patent: Dec. 29, 2020

(54) COMPOUND TO TREAT SJOGREN'S SYNDROME

(71) Applicant: Spectrix Therapeutics, LLC, Southlake, TX (US)

(72) Inventor: Mark Tengler, Southlake, TX (US)

(73) Assignee: Spectrix Therapeutics, LLC, Southlake, TX (US)

( * ) Notice: Subject to any disclaimer, the term of this patent is extended or adjusted under 35 U.S.C. 154(b) by 121 days.

(21) Appl. No.: 16/114,955

(22) Filed: Aug. 28, 2018

(65) Prior Publication Data

US 2019/0060462 A1 Feb. 28, 2019

Related U.S. Application Data

(60) Provisional application No. 62/550,756, filed on Aug. 28, 2017.

(51) Int. Cl.
| | |
|---|---|
| *A61K 9/14* | (2006.01) |
| *A61K 47/32* | (2006.01) |
| *A61K 9/20* | (2006.01) |
| *A61K 9/48* | (2006.01) |
| *A61K 8/81* | (2006.01) |
| *A61K 9/00* | (2006.01) |
| *A61Q 11/00* | (2006.01) |
| *A61P 37/00* | (2006.01) |
| *A61K 31/325* | (2006.01) |
| *A61K 31/4164* | (2006.01) |
| *A61P 1/00* | (2006.01) |
| *A61K 31/439* | (2006.01) |

(52) U.S. Cl.
CPC ............ *A61K 47/32* (2013.01); *A61K 8/8188* (2013.01); *A61K 9/0056* (2013.01); *A61K 9/2027* (2013.01); *A61K 9/4866* (2013.01); *A61Q 11/00* (2013.01); *A61K 9/2054* (2013.01); *A61K 31/325* (2013.01); *A61K 31/4164* (2013.01); *A61K 31/439* (2013.01); *A61K 2300/00* (2013.01); *A61P 1/00* (2018.01); *A61P 37/00* (2018.01)

(58) Field of Classification Search
None
See application file for complete search history.

(56) References Cited

U.S. PATENT DOCUMENTS

| | | | | |
|---|---|---|---|---|
| 5,661,171 | A * | 8/1997 | Acharya | A61K 31/4178 514/397 |
| 6,419,954 | B1 | 7/2002 | Chu et al. | |
| 8,722,632 | B2 | 5/2014 | Cohen et al. | |
| 2002/0176842 | A1 * | 11/2002 | Hughes | A01N 25/10 424/78.12 |
| 2005/0181050 | A1 | 8/2005 | Hirsh et al. | |
| 2006/0029665 | A1 * | 2/2006 | Singh | A61K 9/0058 424/464 |
| 2010/0240591 | A1 | 9/2010 | Glas et al. | |

FOREIGN PATENT DOCUMENTS

EP 2191848 6/2010

OTHER PUBLICATIONS

International Search Report and Written Opinion of PCT/US2018/048327 from the AUPO dated Nov. 28, 2018, 10 pp.
Srikanth, M.V.,et al., "Ion-Exchange Resins as Controlled Drug Delivery Carriers," Journal of Scientific Research, 2010, vol. 2(3), pp. 597-611.

* cited by examiner

*Primary Examiner* — Susan T Tran
(74) *Attorney, Agent, or Firm* — Edwin S. Flores; Chalker Flores, LLP

(57) ABSTRACT

The present invention includes compositions and methods for providing a therapeutically acceptable dose of an active pharmaceutical agent for once a day delivery of the active pharmaceutical compound in an amount effective to treat at least one of: Sjogren's syndrome, Xerostomia, dry mouth, hypo-salivation, or dental carries due to reduced or compromised salivation, wherein both the peak and trough times in the blood level at 8 hours is greater than 25% of the peak value in the blood level concentration.

8 Claims, No Drawings

C OMPOUND TO TREAT SJOGREN'S
SYNDROME

CROSS-REFERENCE TO RELATED
APPLICATIONS

This application claims priority based on U.S. provisional Application No. 62/550,756, filed Aug. 28, 2017, the contents of which is incorporated by reference in its entirety.

STATEMENT OF FEDERALLY FUNDED
RESEARCH

None.

TECHNICAL FIELD OF THE INVENTION

The present invention relates in general to the field of Sjogren's Syndrome, and more particularly, to a novel composition for the treatment of Sjogren's Syndrome.

BACKGROUND OF THE INVENTION

Without limiting the scope of the invention, its background is described in connection with Sjogren's Syndrome.

U.S. Pat. No. 8,722,632, issued to Cohen, et al., entitled, "Methods for treating Sjogren's syndrome by administering a soluble CTLA4 molecule," teaches compositions and methods for treating autoimmune diseases, such as Sjogren's syndrome, by administering to a subject a CTLA4 molecule that block endogenous B7 molecules from binding their ligands.

United States Patent Publication No. 20100240591, filed by Glas, et al., entitled "TPP II inhibitors for use in the treatment of autoimmune and inflammatory diseases and transplant rejection," is said to teach TPP II (tripeptidyl peptidase II) inhibitors are useful in the treatment of autoimmune and/or inflammatory diseases, for example Systemic Lupus Erythematosus, Rheumatoid Arthritis, Multiple Sclerosis, Sjogren's Syndrome, Diabetes Mellitus Type I or II, Psoriasis, Eczema, Ulcerous Colitis, and Charon's Disease, or transplant rejection.

SUMMARY OF THE INVENTION

In one embodiment, the present invention includes a composition comprising: a therapeutically acceptable dose of an active agent for once a day delivery of the active pharmaceutical compound in an amount effective to treat at least one of: Sjogren's syndrome, Xerostomia, dry mouth, hypo-salivation, or dental carries due to reduced or compromised salivation, wherein both the peak and 8 hours blood level concentrations are effective to increase salivation. In one aspect, the active agent is in an active pharmaceutical compound-resin complex. In another aspect, the active agent is at least one of Cevimeline, Pilocarpine, or Bethanechol. In another aspect, the active agent is in an extended-release orally disintegrating tablet (XR-ODT) dosage form or an extended-release chewable (XR-chewable). In another aspect, the resin is a cation exchange resin or a polystyrene sulfonate resin. In another aspect, the composition shows a statistically significantly P<=0.05 improvement in either EULAR Sjögren's syndrome disease activity index (ESSDAI) or EULAR Sjogren's Syndrome Patient Reported Index (ESSPRI) scores compared to placebo over the course of at least 8 hours. In another aspect, the composition further compromises an organic acid. In another aspect, the active agent is in a dosage form selected from at least one of: a chewable tablet, swallowed tablet, a sublingual tablet, a capsule, or a liquid. In another aspect, the composition comprises the formulas set forth in Tables 1 to 6.

In another embodiment, the present invention includes a formulation comprising: a therapeutically effective amount of a pharmaceutically acceptable active agent-ion resin dosage form that provides for a once-daily treatment of at least one of: Sjogren's syndrome, Xerostomia, dry mouth, hypo-salivation, or dental carries due to reduced or compromised salivation, wherein the 8 hour blood level is greater than 25% of the peak value in the blood level concentration. In one aspect, the active agent is at least one of Cevimeline, Pilocarpine, or Bethanechol. In another aspect, the active agent-ion resin dosage form is an XR-ODT dosage form or XR-chewable and the drug resin is a cation exchange resin, or a polystyrene sulfonate. In another aspect, the blood levels for the active agent over the course of 8 hours is greater than 33% of the peak value in the blood level concentration. In another aspect, the blood levels for the active agent at 8 hours is greater than 25% of the peak value in the blood level concentration. In another aspect, the active pharmaceutical shows a statistically significantly P<=0.05 improvement in either EULAR Sjögren's syndrome disease activity index (ESSDAI) or EULAR Sjogren's Syndrome Patient Reported Index (ESSPRI) scores compared to placebo over the course of at least 8 hours. In another aspect, the composition further compromises an organic acid along with the active pharmaceutical composition-ion resin dosage form. In another aspect, the active agent-ion resin dosage form is a chewable tablet, swallowed tablet, a sublingual tablet, a capsule, or a liquid. In another aspect, the formulation comprises the compositions as set forth in Tables 1 to 6.

In yet another embodiment, the present invention includes a method of treating Sjogren's syndrome, Xerostomia, dry mouth, hypo-salivation, or dental carries due to reduced or compromised salivation, comprising: identifying a subject in need of treatment for Sjogren's syndrome, Xerostomia, dry mouth, hypo-salivation, or dental carries due to reduced or compromised salivation; and providing the subject a therapeutically effective amount of a once a day composition comprising an effective amount of the active agent, wherein the blood level at 8 hours is greater than 25% of the peak value. In one aspect, the active agent is at least one of Cevimeline, Pilocarpine, or Bethanechol. In another aspect, the active agent is in a dosage form that is an XR-ODT or XR-chewable dosage form. In another aspect, the active agent is in a dosage form with a drug resin selected from a cation exchange resin, or a polystyrene sulfonate resin. In another aspect, the trough values for the active agent over the course of 8 hours is greater than 25% of the peak value. In another aspect, the active agent further compromises an organic acid along with the active pharmaceutical compound. In another aspect, the active agent is in a dosage form selected from at least one of: a chewable tablet, swallowed tablet, a sublingual tablet, a capsule, or a liquid. In another aspect, both the peak and trough times in the blood level concentrations shows a statistically significantly P<=0.05 improvement in either EULAR Sjögren's syndrome disease activity index (ESSDAI) or EULAR Sjogren's Syndrome Patient Reported Index (ESSPRI) scores compared to placebo over the course of at least 8 hours. In another aspect, the composition comprises the formulas set forth in Tables 1 to 6.

In yet another embodiment, the present invention includes a method of making a formulation comprising: contacting an ion resin with an active agent effective to treat of at least one of: Sjogren's syndrome, Xerostomia, dry mouth, hypo-salivation, or dental carries to form a active agent-ion resin; and forming a dosage form that comprises a therapeutically effective amount of the active agent-ion resin complex in a pharmaceutically acceptable carrier, such that the dosage form provides a once-daily dose that reduces compromised salivation, wherein the blood level at 8 hours is greater than 25% of the peak value.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used herein, the term "pharmaceutically effective amount" refers to that amount of an agent effective to produce the intended effect of reducing, and/or preventing hypo-salivation. Hypo-salivation may be caused by decreased production of salivary fluid.

Pharmaceutical composition refers to a composition suitable for pharmaceutical use in an animal or animal cell line. The animal may be a mammal, such as a human. A pharmaceutical composition of the invention includes a pharmaceutically effective amount of one or more agents to increase salivation or analogs thereof, and optionally a pharmaceutically acceptable resin.

As used herein, the term "flavorant" is intended to mean a compound used to impart a pleasant flavor and often odor to a pharmaceutical preparation. In addition to the natural flavorants, many synthetic flavorants are also used. Such compounds include, by way of example and without limitation, anise oil, cinnamon oil, cocoa, menthol, orange oil, peppermint oil and vanillin and the like.

As used herein, the terms "orally disintegrating tablet", "orally dissolving tablet", or "ODT" refers to a drug dosage form designed and manufactured to dissolve on the tongue rather than swallowed whole. Orally disintegrating tablets have the advantage that they can be taken without water. An extended release-orally disintegrating tablet (XR-ODT) is an ODT that has both an immediate release and an extended release profile, thus providing for once-a-day dosing that greatly increases compliance and has improved therapeutic outcomes. Often, ODTs are provided in conjunction with one or more flavorants and/or taste masking agents that improve the taste of the formulation greater than 10, 20, 30, 40, 50, 60, 70, 80, or 90%. The combination of an active agent an ion exchange resin can be used to enhance taste masking.

As used herein, the term "chewable" refers to semi-soft, palatable and stable chewable treat without addition of water. It should be appreciated to the skilled artisan that a chewable composition will be stable and palatable, fast disintegrating, semi-soft medicated chewable tablets (treats) by extrusion without the addition of extraneous water. A soft chewable tablets does not harden on storage and are resistant to microbial contamination. A semi-soft chewable contain a blend of any one or more of binders, flavours, palatability enhancers, humectants, disintegrating agents, non-aqueous solvents, and diluents that are plasticized with liquid plasticizers, such as glycols and polyols to make them ductile and extrudable. The chewable can be made by extrusion, e.g., including fats or lipids as plasticizers and binding agents, is manufactured in the absence of added water, uses plasticizers to replace water in extrudable matrices, contains humectants to maintain the extruded chewable in a pliant and soft state during its shelf life, or any combination thereof. The chewable form may be provided in conjunction with one or more flavorants and/or taste masking agents that improve the taste of the formulation greater than 10, 20, 30, 40, 50, 60, 70, 80, or 90%. The chewable can include the active agent and the ion exchange resin to enhance taste masking.

As used herein, the term "sweetening agent" is intended to mean a compound used to impart sweetness to a preparation. Such compounds include, by way of example and without limitation, aspartame, dextrose, glycerin, mannitol, erythritol, saccharin sodium, sorbitol and sucrose and the like.

As used herein, the term "tablet antiadherents" is intended to mean agents which prevent the sticking of table formulation ingredients to punches and dies in a tableting machine during production. Such compounds include, by way of example and without limitation, magnesium stearate, talc, and the like.

As used herein, the term "tablet binders" is intended to mean substances used to cause adhesion of powder particles in table granulations. Such compounds include, by way of example and without limitation, acacia, alginic acid, carboxymethyl cellulose, sodium, compressible sugar ethylcellulose, gelatin, liquid glucose, methylcellulose, povidone and pregelatinized starch and the like.

As used herein, the term "tablet and capsule diluent" is intended to mean inert substances used as fillers to create the desired bulk, flow properties, and compression characteristics in the preparation of tablets and capsules. Such compounds include, by way of example and without limitation, dibasic calcium phosphate, kaolin, lactose, mannitol, microcrystalline cellulose, powdered cellulose, precipitated calcium carbonate, sorbitol, and starch and the like.

As used herein, the term "tablet direct compression excipient" is intended to mean a compound used in direct compression tablet formulations. Such compounds include, by way of example and without limitation, dibasic calcium phosphate and the like.

As used herein, the term "tablet disintegrant" is intended to mean a compound used in solid dosage forms to promote the disruption of the solid mass into smaller particles that are more readily dispersed or dissolved. Such compounds include, by way of example and without limitation, alginic acid, carboxymethylcellulose, calcium, microcrystalline cellulose, polacrilin potassium, sodium alginate, sodium starch glycolate, and starch and the like.

As used herein, the term "tablet glidant" is intended to mean agents used in tablet and capsule formulations to reduce friction during tablet compression. Such compounds include, by way of example and without limitation, colloidal silica, cornstarch, talc, and the like.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, zinc stearate, and the like.

As used herein, the term "tablet/capsule opaquant" is intended to mean a compound used to render a capsule or a tablet coating opaque. An opaquant may be used alone or in combination with a colorant. Such compounds include, by way of example and without limitation, titanium dioxide and the like.

As used herein, the term "tablet polishing agent" is intended to mean a compound used to impart an attractive sheen to coated tablets. Such compounds include, by way of example and without limitation, carnauba wax, white wax, and the like.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that (those) named purpose(s) or function(s).

For oral therapeutic administration, the particles containing the active compound(s) may be incorporated with excipients and used in the form of ingestible tablets, buccal tables, troches, capsules, elixirs, suspensions, syrups, wafers, and the like. Such compositions and preparations should contain at least the minimal therapeutic amount per dose. The percentage of the compositions and preparations may, of course, be varied and may conveniently be between about 0.0) 1% to about 80% of the weight of the unit. The amount of particles containing the active compound(s) in such therapeutically useful compositions is such that a suitable dosage will be obtained.

Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2007; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference, and the like, relevant portions incorporated herein by reference.

For example, the one or more agents to increase salivation may be included in a tablet. Tablets may contain, e.g., suitable binders, lubricants, disintegrating agents, coloring agents, flavoring agents, flow-inducing agents and/or melting agents. For example, oral administration may be in a dosage unit form of a tablet, gelcap, caplet or capsule, the active drug component being combined with an non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol, mixtures thereof, and the like. Suitable binders for use with the present invention include: starch, gelatin, natural sugars (e.g., glucose or beta-lactose), corn sweeteners, natural and synthetic gums (e.g., acacia, tragacanth or sodium alginate), carboxymethylcellulose, polyethylene glycol, waxes, and the like. Lubricants for use with the invention may include: sodium oleate, sodium stearate, magnesium stearate, sodium benzoate, sodium acetate, sodium chloride, mixtures thereof, and the like. Disintegrators may include: starch, methyl cellulose, agar, bentonite, xanthan gum, mixtures thereof, and the like.

The active agents that increase salivation or analogs thereof may also be coupled to one or more soluble, biodegradable, bioacceptable polymers as drug carriers or as a prodrug. Such polymers may include: polyvinylpyrrolidone, pyran copolymer, polyhydroxylpropylmethacrylamide-phenol, polyhydroxyethylasparta-midephenol, or polyethylene-oxide-polylysine substituted with palmitoyl residues, mixtures thereof, and the like. Furthermore, the agents to increase salivation or analogs thereof may be coupled one or more biodegradable polymers to achieve controlled release of the agents to increase salivation or analogs thereof, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like. Other examples of polymers for attaching the active agent(s) include, e.g., cation exchange resins or a polystyrene sulfonate resin.

In one embodiment, gelatin capsules (gelcaps) may include the agents to increase salivation or analogs thereof and powdered carriers, such as lactose, starch, cellulose derivatives, magnesium stearate, stearic acid, and the like. Like diluents may be used to make compressed tablets. Both tablets and capsules may be manufactured as immediate-release, mixed-release or modified-release formulations to provide for a range of release of medication over a period of minutes to hours. Compressed tablets may be sugar coated or film coated to mask any unpleasant taste and protect the tablet from the atmosphere. An enteric coating may be used to provide selective disintegration in, e.g., the gastrointestinal tract. Furthermore, these properties can be imparted directly on the particles themselves to achieve the same effect.

For oral administration in a liquid dosage form, the oral drug components may be combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents, mixtures thereof, and the like.

Liquid dosage forms for oral administration may also include coloring and flavoring agents that increase patient acceptance and therefore compliance with a dosing regimen. In general, water, a suitable oil, saline, aqueous dextrose (e.g., glucose, lactose and related sugar solutions) and glycols (e.g., propylene glycol or polyethylene glycols) may be used as suitable carriers for parenteral solutions. Solutions for parenteral administration include generally, a water-soluble salt of the active ingredient, suitable stabilizing agents, and if necessary, buffering salts. Anti-oxidizing agents such as sodium bisulfite, sodium sulfite and/or ascorbic acid, either alone or in combination, are suitable stabilizing agents. Citric acid and its salts and sodium EDTA may also be included to increase stability. In addition, parenteral solutions may include pharmaceutically acceptable preservatives, e.g., benzalkonium chloride, methyl- or propylparaben, and/or chlorobutanol. Suitable pharmaceutical carriers are described in Remington's Pharmaceutical Sciences, Mack Publishing Company, a standard reference text in this field, relevant portions incorporated herein by reference.

Capsules. Capsules may be prepared by filling standard two-piece hard gelatin capsules each with 10 to 500 milligrams of particles containing active ingredient.

Soft Gelatin Capsules. Active particles are suspended in a digestible oil such as soybean oil, cottonseed oil or olive oil. The active particles are prepared and injected by using a positive displacement pump into gelatin to form soft gelatin capsules containing, e.g., an effective amount of one or more agents that increase salivation, e.g., Cevimeline ((2R,5R)-2-methylspiro[1,3-oxathiolane-5,3'-1-azabicyclo[2.2.2]octane]), Pilocarpine ((3S,4R)-3-ethyl-4-[(3-methylimidazol-4-yl) methyl]oxolan-2-one), or Bethanechol (2-[(aminocarbonyl)oxy]-N,N,N-trimethyl-1-propanaminium), including salt forms and derivatives or precursors. The capsules are washed and dried.

Tablets. A large number of tablets are prepared by conventional procedures so that the dosage unit includes an effective amount of one or more agents that increase salivation, e.g., Cevimeline, Pilocarpine, or Bethanechol, 0.2 milligrams of colloidal silicon dioxide, 5 milligrams of magnesium stearate, 50-275 milligrams of microcrystalline cellulose, 11 milligrams of starch and 98.8 milligrams of lactose. Appropriate coatings may be applied to increase palatability or delay absorption.

To provide an effervescent tablet appropriate amounts of, e.g., monosodium citrate and sodium bicarbonate, are blended together and then roller compacted, in the absence of water, to form flakes that are then crushed to give granulates. The granulates are then combined with the agents to increase salivation or analogs thereof, drug and/or salt thereof, conventional beading or filling agents and, optionally, sweeteners, flavors and lubricants.

Injectable solution. A parenteral composition suitable for administration by injection is prepared by stirring 1.5% by weight of agents to increase salivation or analogs thereof in deionized water and mixed with, e.g., up to 10% by volume propylene glycol and water. The solution is made isotonic with sodium chloride and sterilized using, e.g., ultrafiltration.

Suspension. An aqueous suspension is prepared for oral administration so that each 5 ml contain agents that increase salivation, e.g., Cevimeline, Pilocarpine, or Bethanechol or analogs thereof, 200 mg of sodium carboxymethyl cellulose, 5 mg of sodium benzoate, 1.0 g of sorbitol solution, U.S.P., and 0.025 ml of vanillin or suitable flavorant.

For mini-tablets, the active agents to increase salivation are compressed into a tablet with a hardness in the range 0.5 to 12 Kp. The hardness of the final tablets is influenced by the linear roller compaction strength used in preparing the granulates, which are influenced by the particle size of, e.g., the monosodium hydrogen carbonate and sodium hydrogen carbonate. For smaller particle sizes, a linear roller compaction strength of about 15 to 20 KN/cm may be used.

The present invention also includes pharmaceutical kits useful, for example, for the treatment of hypo-salivation, which comprise one or more containers containing a pharmaceutical composition comprising a therapeutically effective amount of the one or more agents to increase salivation. Such kits may further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, may also be included in the kit. It should be understood that although the specified materials and conditions are important in practicing the invention, unspecified materials and conditions are not excluded so long as they do not prevent the benefits of the invention from being realized.

In one example, the present invention includes a pharmaceutical composition comprising active agents for the treatment of Sjogren's syndrome, Xerostomia, dry mouth, hypo-salivation, or dental carries due to reduced or compromised salivation selected from at least one of Cevimeline, Pilocarpine, or Bethanechol, analogs, or equivalents thereof.

The dosages of the present invention can vary to meet the needs of an individual user, or can be produced in large batches having specific amounts of the one or more active pharmaceutical agents for once a day delivery of the active pharmaceutical compound to treat at least one of: Sjogren's syndrome, Xerostomia, dry mouth, hypo-salivation, or dental carries due to reduced or compromised salivation or equivalents thereof based on the most commonly used amounts. For example, the amount of the one or more active pharmaceutical agents for once a day delivery of the active pharmaceutical compound to treat at least one of: Sjogren's syndrome, Xerostomia, dry mouth, hypo-salivation, or dental carries due to reduced or compromised salivation can be Cevimeline, Pilocarpine, or Bethanechol per dose.

The ionic exchange resin and coating can be selected such that less than 20, 23, 30, 35, 40, 45, 50, 55, or 60% of the Cevimeline, Pilocarpine, and/or Bethanechol is released within the first 45 minutes after the product is introduced into an in vitro dissolution assay, wherein the conditions of the dissolution assay are an initial dissolution medium of 0.1 N HCL, and after 2 hours, the medium is adjusted to a pH of about 6.8; and the dissolution assay is performed using a USP Apparatus 2.

Another example of the present invention includes a pharmaceutical composition comprising Cevimeline, Pilocarpine, or Bethanechol complexed with ion-exchange resin particles to form drug resin particles, wherein the composition comprises a first plurality of immediate release drug-resin particles and a second plurality of drug-resin particles that are coated for modified release coating, wherein the composition has an in vivo fasted serum profile with a first and second peak wherein the first peak occurs before 3 hours after ingestion of the composition and the second peak occurs after 3 hours after ingestion.

Another example of the present invention includes a method of making a pharmaceutical composition comprising: attaching one or more Cevimeline, Pilocarpine, and/or Bethanechol or analogs thereof with ion-exchange resin particles to form drug-resin particles, wherein at least 20, 25, 30, 35 or 40% by weight of a first active agent, such as, Cevimeline, Pilocarpine, and/or Bethanechol or more is formulated for immediate release; and a second active agent, such as, Cevimeline, Pilocarpine, and/or Bethanechol is formulated for modified release. The amounts of each of the, e.g., Cevimeline, Pilocarpine, and/or Bethanechol can be varied depending on the final formulation, and when used in combination, e.g., Cevimeline is generally provided at 10-60 milligrams, Pilocarpine is generally provided at 2.5-15 milligrams, and/or Bethanechol is generally provided at 5-125 milligrams, however, when used in combination the relative ratio of each, weight-to-weight, may be varied, e.g., each can be between 5, 10, 20, 25, 30, 33, 40, 50, 60, 66, 70, 75, 80, 90, or 95% of the final formulation, with each of the other active agents making up the balance of the active agent to 100%, with each component being used at its therapeutic amount for once a day administration.

Another example of the present invention includes a method of evaluating a formulation believed to be useful in treating Sjogren's syndrome, Xerostomia, dry mouth, hypo-salivation, or dental carries due to reduced or compromised salivation, the method comprising: a) measuring the blood levels of one or more active agents from a first set of subjects suspected of having Sjogren's syndrome, Xerostomia, dry mouth, hypo-salivation, or dental carries due to reduced or compromised salivation; b) administering the formulation to a first subset of the patients, and a placebo to a second subset of the patients; c) repeating step a) after the administration of the formulation or the placebo; and d) determining if the formulation reduces the number of Sjogren's syndrome, Xerostomia, dry mouth, hypo-salivation, or dental carries due to reduced or compromised salivation that is statistically significant as compared to any reduction occurring in the second subset of patients, wherein a statistically significant reduction indicates that the formulation is useful in treating Sjogren's syndrome, Xerostomia, dry mouth, hypo-salivation, or dental carries due to reduced or compromised salivation.

TABLE 1

Oral Disintegrating Tablet (ODT) Cevimeline
Example Formulation #1 ODT Cevimeline

| Ingredient | Function | Amount per dose (mg) low | high | |
|---|---|---|---|---|
| Cevimeline HCl | Active | 10.0 | 60.0 | |
| Polistirex exchange Resin | Exchange Resin | 20.00 | 210.0 | |
| Methacrylic Acid | DR polymer | 8.0 | 84.0 | Can be used |
| Ethylcellulose | XR polymer | 2.0 | 84.0 | together or separately |
| Mannitol | | 40.0 | 240.0 | |
| Crospovidone | | 6.0 | 36.0 | |
| Microcrystalline Cellulose | | 4.0 | 24.0 | |
| Fructose | | 6.0 | 36.0 | |
| Flavoring | | 2.0 | 10.0 | |
| Colloidal Silicon Dioxide | | 2.0 | 12.0 | |
| Triethyl Citrate | | 2.0 | 8.0 | |
| Sucralose | | 2.0 | 8.0 | |
| Lake Blend Coloring | | 0.4 | 2.0 | |
| Magnesium Stearate | | 0.4 | 2.0 | |
| Polyethylene Glycol | | 0.2 | 1.0 | |

TABLE 2

Tablet Cevimeline
Example Formulation #1 Tablet Cevimeline

| Ingredient | Function | Amount per dose (mg) low | high | |
|---|---|---|---|---|
| Cevimeline HCl | Active | 10.0 | 60.0 | |
| Polistirex exchange Resin | Exchange Resin | 20.0 | 210.0 | |
| Methacrylic Acid | DR polymer | 8.0 | 84.000 | Can be used |
| Ethylcellulose | XR polymer | 2.0 | 84.000 | together or separately |
| Dibasic Calcium Phosphate | | 30.0 | 300.0 | |
| Glyceryl Behenate | | 10.0 | 100.0 | |
| Stearyl Alcohol | | 20.0 | 200.0 | |
| Micro Crystalline Cellulose | | 30.0 | 300.0 | |
| Magnesium Stearate | | 0.4 | 2.0 | |
| Polyethylene Glycol | | 0.2 | 1.0 | |

TABLE 3

ODT Tablet Pilocarpine
Example Formulation #2 ODT Tablet Pilocarpine

| Ingredient | Function | Amount per dose (mg) low | high | |
|---|---|---|---|---|
| Pilocarpine HCl | Active | 2.5 | 15.0 | |
| Polistirex exchange Resin | Exchange Resin | 5.00 | 60.0 | |
| Methacrylic Acid | DR polymer | 2.0 | 24.0 | Can be used |
| Ethylcellulose | XR polymer | 0.5 | 24.0 | together or separately |
| Mannitol | | 40.0 | 240.0 | |
| Crospovidone | | 6.0 | 36.0 | |
| Microcrystalline Cellulose | | 4.0 | 24.0 | |
| Fructose | | 6.0 | 36.0 | |
| Flavoring | | 2.0 | 10.0 | |
| Colloidal Silicon Dioxide | | 2.0 | 12.0 | |
| Triethyl Citrate | | 2.0 | 8.0 | |
| Sucralose | | 2.0 | 8.0 | |
| Lake Blend Coloring | | 0.4 | 2.0 | |
| Magnesium Stearate | | 0.4 | 2.0 | |
| Polyethylene Glycol | | 0.2 | 1.0 | |

TABLE 4

Tablet Pilocarpine
Example Formulation #2 Tablet Pilocarpine

| Ingredient | Function | Amount per dose (mg) low | high | |
|---|---|---|---|---|
| Pilocarpine HCl | Active | 2.5 | 15.0 | |
| Polistirex exchange Resin | Exchange Resin | 5.0 | 60.0 | |
| Methacrylic Acid | DR polymer | 2.0 | 24.000 | Can be used |
| Ethylcellulose | XR polymer | 0.5 | 24.000 | together or separately |
| Dibasic Calcium Phosphate | | 30.0 | 300.0 | |
| Glyceryl Behenate | | 10.0 | 100.0 | |
| Stearyl Alcohol | | 20.0 | 200.0 | |
| Micro Crystalline Cellulose | | 30.0 | 300.0 | |

TABLE 4-continued

Tablet Pilocarpine
Example Formulation #2 Tablet Pilocarpine

| Ingredient | Function | Amount per dose (mg) low | high |
|---|---|---|---|
| Magnesium Stearate | | 0.4 | 2.0 |
| Polyethylene Glycol | | 0.2 | 1.0 |

TABLE 5

ODT Tablet Bethanechol
Example Formulation #2 ODT Tablet Bethanechol

| Ingredient | Function | Amount per dose (mg) low | high | |
|---|---|---|---|---|
| Bethanechol Cl | Active | 5.0 | 125.0 | |
| Polistirex exchange Resin | Exchange Resin | 10.00 | 300.0 | |
| Methacrylic Acid | DR polymer | 4.0 | 120.0 | Can be |
| Ethylcellulose | XR polymer | 1.0 | 120.0 | used together or separately |
| Mannitol | | 40.0 | 240.0 | |
| Crospovidone | | 6.0 | 36.0 | |
| Microcrystalline Cellulose | | 4.0 | 24.0 | |
| Fructose | | 6.0 | 36.0 | |
| Flavoring | | 2.0 | 10.0 | |
| Colloidal Silicon Dioxide | | 2.0 | 12.0 | |
| Triethyl Citrate | | 2.0 | 8.0 | |
| Sucralose | | 2.0 | 8.0 | |
| Lake Blend Coloring | | 0.4 | 2.0 | |
| Magnesium Stearate | | 0.4 | 2.0 | |
| Polyethylene Glycol | | 0.2 | 1.0 | |

TABLE 6

Tablet Bethanechol
Example Formulation #2 Tablet Bethanechol

| Ingredient | Function | Amount per dose (mg) low | high | |
|---|---|---|---|---|
| Bethanechol Cl | Active | 5.0 | 125.0 | |
| Polistirex exchange Resin | Exchange Resin | 10.0 | 300.0 | |
| Methacrylic Acid | DR polymer | 4.0 | 120.000 | Can be |
| Ethylcellulose | XR polymer | 1.0 | 120.000 | used together or separately |
| Dibasic Calcium Phosphate | | 30.0 | 300.0 | |
| Glyceryl Behenate | | 10.0 | 100.0 | |
| Stearyl Alcohol | | 20.0 | 200.0 | |
| Micro Crystalline Cellulose | | 30.0 | 300.0 | |
| Magnesium Stearate | | 0.4 | 2.0 | |
| Polyethylene Glycol | | 0.2 | 1.0 | |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of treating Sjogren's syndrome, Xerostomia, dry mouth, hypo-salivation, or dental carries due to reduced or compromised salivation, comprising:
    identifying a subject in need of treatment for Sjogren's syndrome, Xerostomia, dry mouth, hypo-salivation, or dental carries due to reduced or compromised salivation; and
    providing the subject a therapeutically effective amount of a once a day composition comprising an effective amount of an active agent selected from the group consisting of Cevimeline, Pilocarpine, and Bethanechol,
    wherein the active agent complexed with ion-exchange resin particles to form drug resin particles,
    wherein the composition comprises a first plurality of immediate release drug-resin particles and a second plurality of drug-resin particles that are coated for modified release coating, and
    wherein the composition has an in vivo fasted serum profile with a first and a second peak, wherein the first peak occurs before 3 hours after ingestion of the composition and the second peak occurs after 3 hours after ingestion.

2. The method of claim 1, wherein the active agent is in a dosage form that is an XR-ODT or XR-chewable dosage form.

3. The method of claim 1, wherein the active agent is in a dosage form with a drug resin selected from a cation exchange resin, or a polystyrene sulfonate resin.

4. The method of claim 1, wherein the trough values for the active agent over the course of 8 hours is greater than 25% of the peak value.

5. The method of claim 1, wherein the active agent further compromises an organic acid along with the active pharmaceutical compound.

6. The method of claim 1, wherein the active agent is in a dosage form selected from at least one of: a chewable tablet, swallowed tablet, a sublingual tablet, a capsule, or a liquid.

7. The method of claim 1, wherein both the peak and trough times in the blood level concentrations shows a statistically significantly $P \leq 0.05$ improvement in either EULAR Sjogren's syndrome disease activity index (ESSDAI) or EULAR Sjogren's Syndrome Patient Reported Index (ESSPRI) scores compared to placebo over the course of at least 8 hours.

8. The method of claim 1, the composition comprises the formulas set forth in Tables 1 to 6.

* * * * *